US00PP12068P2

(12) United States Plant Patent
Jacobs

(10) Patent No.: US PP12,068 P2
(45) Date of Patent: Aug. 28, 2001

(54) ***LIRIOPE GIGANTEA* PLANT NAMED 'MERTON JACOBS'**

(75) Inventor: Randall Merton Jacobs, Bushnell, FL (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 09/419,939

(22) Filed: Oct. 18, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A. Para

(57) ABSTRACT

A new and distinct *Liriope gigantea* plant found as an openly pollinated seedling. The new variety is distinct with its dark foliage, increased vigor and increased raceme length.

1 Drawing Sheet

BACKGROUND OF THE INVENTION

This new Liriope variety was found as an openly pollinated seedling of *Liriope gigantea* maintained by Flowerwood Nursery, Inc. in Bushnell, Fla. The plant upon which the seed of *Liriope gigantea* 'Merton Jacobs' was found is not a horticultural variety or cultivar and is not patented or available commercially. The seedling, hereinafter referred to as 'Merton Jacobs' was discovered by Randall Merton Jacobs in 1994. The value of this new cultivar lies in its unique dark green foliage, increased growth rate, and unique display of flowers above the foliage.

Asexual propagation of the new plant by division has been under Mr. Jacobs' direction at the same location. Several generations of the new plant have been evaluated and the distinctive characteristics of the plant have remained stable. The plant cannot be reproduced true from seed.

SUMMARY OF THE INVENTION

The following are the most outstanding and distinguishing characteristics of this new cultivar when grown under normal horticultural practices in Bushnell, Fla.

1. Attractive violet flowers are produced on long racemes.
2. Foliage is dark green year round.
3. Fast growth rate under normal fertilization and moisture conditions.
4. Form is grasslike when leaves recurving toward the ground.
5. Easily propagated by division.
6. Heat and drought resistant.
7. Good groundcover.
8. Tolerates full sun to shade.
9. Desirabe in planters.
10. Effective in mass.
11. Withstands wind and salt spray.
12. An excellent plant for borders.
13. Hardy to Zone 8.

DESCRIPTION OF THE DRAWINGS

This new *Liriope gigantea* variety is illustrated by the acompanying photographic prints in which.

1.

2.

Figure 1:
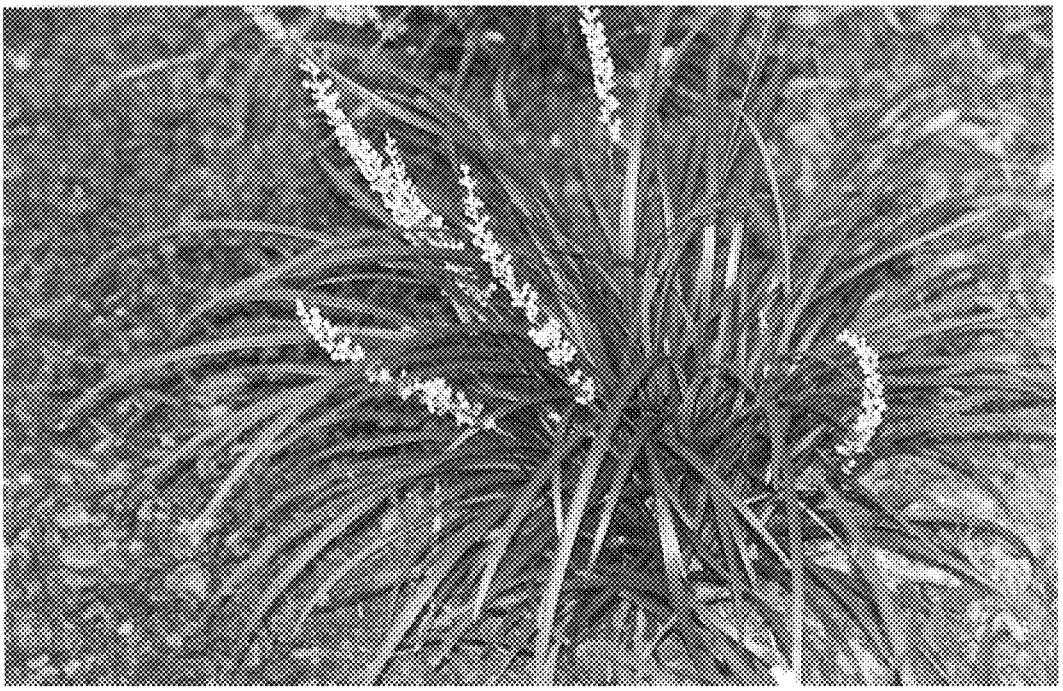
FIG. 1 is a close-up of the new variety 'Merton Jacobs' showing the violet flowers on long racemes and the grasslike dark green foliage.
Figure 2:
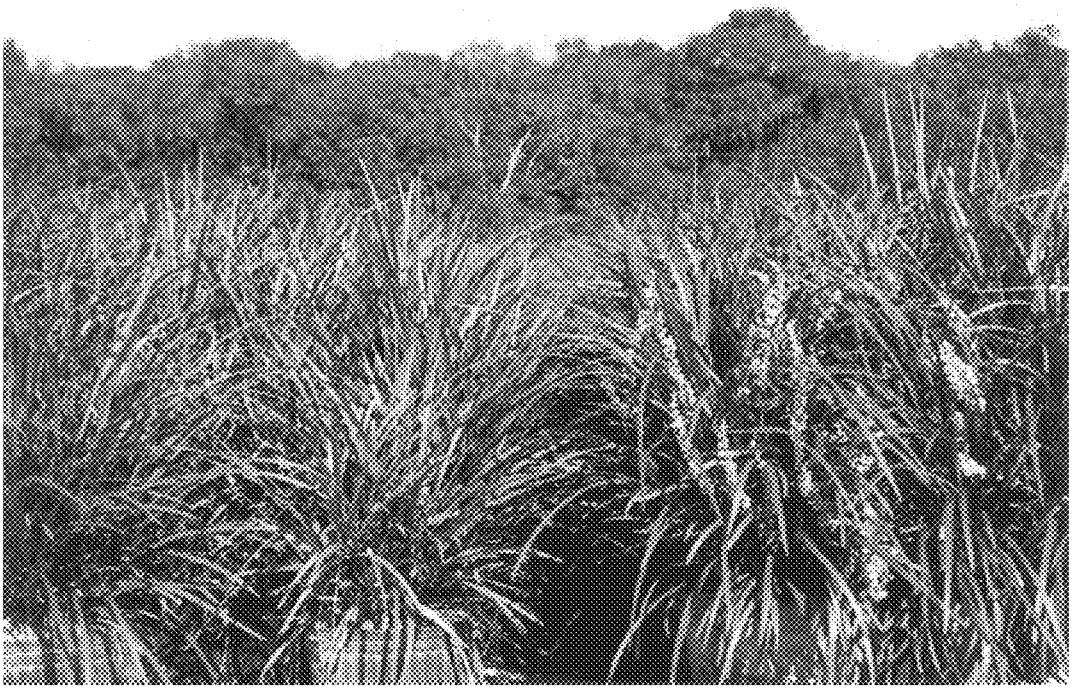
FIG. 2 is a side-by-side photograph of the species *Liriope gigantea* (on the left) and the new variety 'Merton Jacobs' (on the right). This photograph, which was taken in mid-August, shows the attractive flowers and dark green foliage of the new variety.

Ths colors shown are as true as is reasonably possible to obtain by conventional photographic procedures. The colors of the various plant parts are defined with reference to The Royal Horticultural Society Color Chart. Description of colors in ordinary terms are presented where appropriate for clarity in meaning.

BOTANICAL DESCRIPTION OF THE PLANT

The following is a detailed description of the new variety of Liriope based on my observations made of plants grown in wholesale commercial production practices, in greenhouses, and in established landscape plantings at Flowerwood Nursery, Inc. in Bushnell, Fla.

Dinstinctive Characteristics:

| Characteristic | Liriope g. 'Merton Jacobs' | *Liriope gigantea* (The species) |
|---|---|---|
| Height (Mature) | 24– 30" | 24– 30" |
| Width (Mature) | 24– 30" | 24– 30" |
| Bloom Period | Aug– Sept. | Sept.– Oct. |
| Racema Length | 14– 18" | 6– 10" |
| Leaf Length | 1– 3' | 1– 3' |
| Leaf Width | 5/16– 7/16" | 3/8– 5/8" |
| Leaf Color (Mature) | Green G. 137A | Green G. 137B |

Classification:

*Botanic.*—*Liriope gigantea* 'Merton Jacobs'.

*Form.*—Dense, grasslike clump.

*Size.*—In a period of three years from a division, under normal growing conditions in Bushnell, Fla., the plant reaches a height of 18 to 20" and a spread of 18 to 20". The plant normally grows at a rate of about 6" or more per year and reaches a height of 30" and a spread of 30" at maturity. Many leaves arise from a central crown resulting in a dense habit. The parent species obtains similar height and spread over this period of time, however it produces approximately 40% fewer leaves resulting in a much thinner plant.

*Foliage.*—Evergreen, grasslike, basal, rhizomatous, coriaceous, narrowly linear, margins smooth, firm, ascending to arching, long alternate, 5/16" to 7/16" wide by 1 to 3' long. Leaves are numerous and leaf veination is parallel. The upper surface of the immature leaves is Green Group 143A, glossy and glabrous. The underside is Green Group 137C and matte. The veins are Green Group 137A and between the veins are Green Group 137D. The upper surface of the mature leaves is Green Group 137A, glossy and glabrous and the underside remains Green Group 137C and matte. The base of the leaves is Yellow-Green Group 145A.

Like the parent species, 'Merton Jacobs' has no above ground stems. It grows by adding bibs or small clumps of leaves on short rhizomes on the side of the existing clump. The rhizomes are normally less than one inch long. As the plant grows, the clump becomes larger and can be propagated by separating the bibs. Sections of the fibrous root system often enlarge and function as food storage organs. These rhizomes are ½ to ¾" long, ¼ to ½" wide, Yellow-White Group 158B and are not useful for propagation.

In 1997, the date of initial spring growth was March 7, in Bushnell, Fla. After the initial spring flush, there was almost continuous growth until fall, ending October 27, also in Bushnell, Fla. This growth pattern was identical to the parent species, however, the 'Merton Jacobs' clumps increase in size quicker than the parent species. This increased vigor may result from a higher level of chlorophyll in the new plant as evident by the darker green foliage.

Flowers: Perfect, fragrant, in axillary fascicles arranged in terminal racemes. The flowers and mature buds are Violet Group 85B. The pedicel is ⅛ to 3/16" long and Violet Group 85D. Immature buds are White Group 155C. There are six to eight elliptical petals which are ¼" long and ⅛" wide. No sepals are produced. The six stamens are 1/16" long and the superior ovary is 3/32" long. The pollen is Yellow Group 3B. Flowers are borne on racemes in clusters of 3 to 5, which are open from the base to the apex and are held high in the foliage. Each cluster emerges from a bract which is Green Group 143C. The racemes are 14 to 18" long and have a 1/16 to ⅛" diameter. These racemes are Purple Group 79D at the base and Purple Group 76A near the apex. There is a six to eight week flowering period normally beginning in early August in Bushnell, Fla. A mature plant may have 50 or more racemes producing several hundred flowers. Flowers have a sweet fragrance.

Fruit: Berrylike drupe, globose, 3/16 to 5/16" diameter, containing one or two seeds ⅛ to ¼" diameter, globose, and Greyed-Green Group 196A. Immature fruit are Yellow-Green Group 144B maturing to Green Group 139A. In the late fall and early winter the fruit turn black Group 202A and fall off. Fruit set may be heavy.

Culture: Grows well in a wide range of conditions and tolerates sun to shade. Grows in nearly any soil type, from moist to dry and sand to clay. Very heavy clays should be amended with peat moss, compost, or shredded pine bark to improve the soil texture. Poorly drained locations should be avoided. Responds well to mulching and medium applications of fertilizer; prefers ph 6 to 7. Adaptable to containers and above ground planters. Tolerates wind and salt spray. Propagated by division any time of year. Cold hardiness and resistance to drought, insects, and disease are comparable to the parent species.

Pests: None serious.

I claim:

1. A new and distinct variety of Liriope plant named 'Merton Jacobs', as illustrated and described.

* * * * *